(12) United States Patent
Ferrini

(10) Patent No.: US 9,139,490 B2
(45) Date of Patent: Sep. 22, 2015

(54) PROCESS FOR THE PRODUCTION OF LIGHT OLEFINS FROM SYNTHESIS GAS

(71) Applicant: Casale SA, Lugano (CH)

(72) Inventor: Cristina Ferrini, Breganzona (CH)

(73) Assignee: Casale SA (CH)

( * ) Notice: Subject to any disclaimer, the term of this patent is extended or adjusted under 35 U.S.C. 154(b) by 0 days.

(21) Appl. No.: 14/510,899

(22) Filed: Oct. 9, 2014

(65) Prior Publication Data

US 2015/0025160 A1 Jan. 22, 2015

Related U.S. Application Data

(63) Continuation of application No. 13/695,743, filed as application No. PCT/EP2011/057307 on May 6, 2011, now abandoned.

(30) Foreign Application Priority Data

May 10, 2010 (EP) .................................... 10162438

(51) Int. Cl.
*C07C 27/00* (2006.01)
*C07C 1/04* (2006.01)

(52) U.S. Cl.
CPC .............. *C07C 1/044* (2013.01); *C07C 2521/04* (2013.01); *C07C 2521/06* (2013.01); *C07C 2521/08* (2013.01); *C07C 2521/10* (2013.01); *C07C 2521/12* (2013.01); *C07C 2523/745* (2013.01); *C07C 2523/78* (2013.01)

(58) Field of Classification Search
CPC ........ C07C 1/044; C07C 11/04; C07C 11/06; C07C 2521/04; C07C 2521/06; C07C 2521/10; C07C 2521/12; C07C 2523/78
USPC .......................................... 518/700, 719, 721
See application file for complete search history.

(56) References Cited

U.S. PATENT DOCUMENTS

| 4,463,101 | A | 7/1984 | Dwyer et al. |
| 7,199,077 | B2 | 4/2007 | Hu et al. |
| 2002/0032244 | A1 | 3/2002 | Benham et al. |
| 2009/0202417 | A1 | 8/2009 | Carpenter |
| 2010/0261940 | A1 | 10/2010 | Jun et al. |

FOREIGN PATENT DOCUMENTS

| CN | 1083415 A | 3/1994 |
| CN | 101396662 A | 4/2009 |
| WO | WO 2011/027921 A2 * | 3/2011 |

OTHER PUBLICATIONS

Zhang et al., Chemical Abstract CN 101396662, Apr. 2009.*
Zhou Jun, Chu Wei, et al. "Effects of Different MgO Supports on FeMn Based Catalysts for Light Alkenes Synthesis", Journal of Fuel Chemistry and Technology, Apr. 2009, vol. 37, No. 2, pp. 222-226.
International Search Report issued in connection with PCT/EP2011/057307, 2011.
International Preliminary Report on Patentability issued in connection with PCT/EP2011/057307, 2011.
Response to Written Opinion dated Aug. 29, 2012 in connection with PCT/EP2011/057307.
Response to Written Opinion dated Mar. 12, 2012 in connection with PCT/EP2011/057307.
Zhang et al., "Preparation of Multicomponent Iron Base Ultrafine Particle Catalyst and Theri Catalytical Properties", Chinese Journal of Catalysis, vol. 19, No. 1, pp. 63-66, Jan. 31, 1998.

* cited by examiner

*Primary Examiner* — Jafar Parsa
(74) *Attorney, Agent, or Firm* — Akerman LLP

(57) ABSTRACT

A new process for light-olefins production is disclosed. The process comprises the step of contacting syngas with a iron-based catalyst at a temperature in the range from 250° C. to 350° C. and at a pressure in the range from 10 bar to 40 bar. By so doing a production of light olefins with a selectivity of at least 80% is obtained.

15 Claims, No Drawings

PROCESS FOR THE PRODUCTION OF LIGHT OLEFINS FROM SYNTHESIS GAS

CROSS-REFERENCE TO RELATED APPLICATIONS

This application is a continuation of U.S. patent application Ser. No. 13/695,743, filed Nov. 1, 2012, which is a national phase of PCT/EP2011/057307, filed May 6, 2011, which claims priority to European Patent Application No. 10162438.5, filed May 10, 2010. The entire contents of these applications is incorporated herein by reference.

FIELD OF APPLICATION

In its most general aspect, the present invention relates to the production of light olefins, such as ethylene and propylene.

In particular, the present invention relates to a new process for preparing light olefins, such as $C_{2-4}$ olefins, with high yield and selectivity from synthesis gas.

PRIOR ART

The conversion of hydrocarbons into light olefins such as ethylene and propylene is an important industrial process as light olefins are valuable starting chemicals widely used in the production of several materials as plastics and polyolefins products such as polyethylene, polypropylene and co-polymers thereof.

Important sources of hydrocarbons for conversion include natural gas as well as refinery gases such as naphtha or other oil-based products.

In one industrial process, which is the more widely used worldwide, light olefins such as $C_{2-4}$ olefins, are produced by steam cracking or fluid catalytic cracking of cracker feedstocks composed of naphtha hydrocarbons.

The yield of light olefins, particularly of ethylene from a naphtha cracker depends upon the hydrocarbon content in the feed. Ethylene yields are highest when the feed is composed of high concentrations of paraffins, particularly linear paraffins. However, only limited supplies of highly linear paraffin feedstocks are available from petroleum refineries.

In addition, it should be considered that the cost of oil and oil-based products have increased in the last years and is expected to increase further in the future and this has driven the search for alternative processes to produce hydrocarbons starting from other sources, such as natural gas, coal and renewable sources as biomass.

In this connection, regarding the production of light olefins, another industrial process has been developed which involves the initial production of synthesis gas (syngas), mainly including carbon oxide (CO) and hydrogen (H2) and then conversion of syngas into methanol which is in turn converted into light olefins.

The syngas may be easily obtained from non oil-based sources, in particular natural gas which can be converted to syngas through conventional steam reforming processes.

It is also known in the art to produce syngas by converting a variety of feedstocks, such as coal and renewable sources, i.e. biomass such as corn stover, switchgrass, sugar cane bagasse, sawdust, and the like, black liquor, and lignin to synthesis gas. The water-gas-shift react plays an important role in the conversion of certain of these feedstocks to hydrogen via steam gasification and pyrolysis. Catalytic steam gasification can give high yields of syngas at relatively low temperatures.

The syngas can be converted to methanol through conventional processes and the resulting methanol can be transported to existing plants for light olefins production or used in an integrated plant for methanol and light olefins production, where methanol is converted into light olefin through conventional methanol to olefins (MTO) processes.

MTO processes are also well known in art and usually allow to obtain light olefins, particularly ethylene and propylene with relativity high yield and high selectivity which can usually be more than 80%.

As known, MTO processes need to use appropriate catalysts for the conversion among which the more widely used are silicolaluminophosphates (SAPOs) materials, in particular SAPO-34.

SAPO materials may be prepared by reacting appropriate sources of Al, Si and P in the presence of a structure-directing agent (template) under specific ratios and conditions.

However, the synthesis of SAPO materials is highly critical. Sometimes, it is observed that, even using the same reactants, different materials may be obtained depending on the synthesis path used, these materials having same chemical composition and SAPO structure as identified by X-ray diffraction but different catalytic properties.

In addition, SAPO materials are costly due in particular to the high cost of the template, thereby the overall process for light olefins production starting from syngas and involving a MTO process is often not cost-effective compared to the conventional cracking processes of oil-based products such as naphtha.

This strongly limits the applicability MTO processes to an industrial level even if light olefins may be obtained at relatively high yield and selectivity.

The technical problem underlying the present invention is then that of providing a process for light olefin production from non-oil sources which allow to obtain light olefins with high yield and selectivity while involving low costs so as to be applicable to an industrial level.

SUMMARY OF INVENTION

It has been now found out that light olefins can be produced with relatively high yield and selectivity from a direct conversion of syngas to light olefins without forming the intermediate methanol that is then to be converted to light olefins through a MTO process.

According to the invention, the above-mentioned technical problem is solved by a process for light-olefins production comprising the step of contacting syngas with a iron-based catalyst at a temperature in the range from 250° C. to 350° C., and at a pressure in the range from 10 bar to 40 bar.

Thanks to the present invention, it is advantageously obtained a production of light olefins with a selectivity of at least 80%.

DETAILED DESCRIPTION OF THE INVENTION

In the following description, the term "light olefins" means unsaturated hydrocarbons C2-C4, particularly ethylene and propene.

In addition, the term "synthesis gas or syngas" means a gas mixture mainly comprising CO and H2 obtained by conversion of non-oil sources.

In particular, the syngas may be obtained by converting natural gas through conventional steam reforming processes or by converting other non-oil sources, in particular coal or renewable sources such as biomass through conventional processes.

Depending on the quality of the syngas, it may be desirable to purify the syngas prior to the conversion to light olefins according to the invention to remove carbon dioxide produced during the syngas reaction, and any sulfur compounds, if they have not already been removed. In particular, sulphur is a strong poison for the iron-based catalyst and should be removed as much as possible, for instance to a sulphur content in the syngas to be converted lower than 1 ppm.

This can be accomplished by contacting the syngas with a mildly alkaline solution (e.g., aqueous potassium carbonate) in a packed column.

According to the invention, the term "high selectivity" means a content of $C_{2-4}$ olefins, particularly ethylene and propylene, in gaseous reaction products obtained from the conversion of syngas on iron-based catalyst under the conditions of the invention, of at least 80% by weight, preferably 85-90% by weight.

According to a preferred embodiment of the invention, the direct conversion of syngas to light olefins is carried out at a temperature in the range from 300° C. to 350° C. and at a pressure in the range from 10 bar to 40 bar.

The syngas may have a H2:CO molar ratio in the range from 1.5 to 2.5. The syngas may contain up to 5.% of inert gaseous components.

Preferably, the syngas has a H2:CO molar ratio around 2:1.

Without being bound to a theory, it is believed that the direct conversion of syngas to light olefins involves the following reactions:

$$nCO + 2nH_2 \rightarrow C_nH_{2n} + nH_2O \text{ (grow chain reaction)}$$

$$CO + H_2O \rightarrow H_2 + CO_2 \text{ (shift reaction)}$$

The first reaction is conventionally known as Fischer-Tropsch (FT) reaction but, as known in the art, it provides liquid fuels, such as gasoline ($C_5$-$C_{11}$) and diesel ($C_9$-$C_{25}$).

However, according to the invention, it has been found out, surprisingly, that grow chain in the FT reaction can be relatively low by using a iron-based catalyst in the FT reaction and operating the FT reaction at a temperature from 250° C. to 350° C. and at a pressure in the range from 10 bar to 40 bar. This advantageously allows to shift the selectivity of the syngas conversion towards light olefins.

In the process according to the invention, such selectivity for light olefins is fully comparable to that obtained from MTO processes and it is at least 80% and preferably between 85% and 90%.

Iron-based catalysts are commonly used in ammonia synthesis processes from hydrogen and nitrogen as disclosed for example in the US patent application No. 2009/0202417.

In the process according to the invention, the catalyst includes iron and/or iron oxides particles as active component(s) which may be arranged on a metal oxide support or matrix. Suitable metal oxide supports or matrices which can be used include alumina, titania, silica, magnesium oxide, silica-alumina, ferrous materials such as magnetite, wustite, cordierite and the like, and mixtures thereof.

The catalyst may also contain a promoter of the catalytic activity. The promoter may be chosen from elements, molecules/compounds and combinations thereof including: aluminium, potassium, calcium, magnesium, silicon, manganese and copper.

Preferably, the catalyst may comprise one or more promoters chosen from the list indicated above in a percentage of 0.1-5% by weight on the weight of the support or matrix. If the content of promoter(s) is less than 0.1%, the production of methane and paraffin may increase. In contrast, if the content of promoter(s) exceeds 5%, reaction activity and olefin yield are not significantly increased.

The most preferred promoters for catalylic activity used in the present invention are elements, molecules/compounds and combination thereof including manganese, potassium and copper.

In this connection, potassium and copper promoters allows to increase adsorption of CO on the metal surface (the metal being iron (Fe) and/or iron oxides (FeOx)) providing an electron donor, thereby enhancing the grow chain reaction rate.

Manganese compounds, in particular manganese oxide (MnO), are very useful as they increase the selectivity of the FT reaction to light olefins.

A particularly preferred iron-based catalyst including manganese (Mn) and potassium (K) promoters is particularly preferred in the process of the invention as it allows enhancing the selectivity for light olefins up to 85-90%.

The preparation of the iron-based catalyst used in the process according to the invention can be carried out by conventional processes normally used for preparing iron catalysts for ammonia synthesis. Such processes include precipitation of Fe particles onto the catalyst support or melting processes.

A suitable melting process involves melting of a Fe compound such as magnetite (Fe3O4) optionally with promoter compounds followed by cooling and solidification. The resulting porous material is then crushed into granules at the desired size. Active catalyst is then produced by reduction of iron oxides with hydrogen and nitrogen gas mixture, to give porous iron and unreduced promoter oxides.

The size of the iron-based catalyst used in the present invention may be preferably in the range of 1-10 millimeters.

A particularly preferred catalyst includes nano-sized Fe particles as active component.

As used herein nano-sized Fe particles means Fe nano-particles, Fe alloy nano-particles, nano-particles having an iron or iron alloy core and an iron-oxide shell or mixtures thereof.

Preferably, the content of nano-sized Fe particles is comprised between 1% and 5% by weight on the weight of the support or matrix.

The particles are preferably substantially spherical and have preferably a diameter less than about 50 nm, more preferably between about 15 and 25 nm, and most preferably between about 1 and 15 nm.

These particles can be produced through conventional processes for example by vapor condensation in a vacuum chamber as disclosed in the U.S. Pat. No. 7,282,167.

The nano-sized iron catalyst particles are disposed on a support material configured to disperse or separate the particles. In this way, iron sintering could be minimized and catalysis efficiency could be maintained over time.

The process according to the invention can be carried out in a variety of reactors for example, fixed bed reactors containing one or more catalyst beds, slurry reactors, fluidized bed reactors, or a combination of different type reactors.

The catalyst may also be activated prior to use in a conventional manner. This may be accomplished for example by reducing the catalyst under hydrogen atmosphere at 350-550° C. and normal pressure for 1-24 hours.

As the FT reaction is highly exothermic, the process according to the invention may also include the step of removing the reaction heat in a continuous or discontinuous way. This may be accomplished by using reactors equipped with appropriate cooling means such as cooling plates internally crossed by a cooling fluid.

In this way, local overheating in the reactor is avoided which may compromise the catalytic activity and/or may promote Fe sintering.

The present invention will be now described with reference to the following examples that are given for indicative and non-limiting purpose.

Example 1

Direct conversion of syngas to light-olefins was performed using a catalyst containing nano-sized Fe particles dispersed on a matrix consisting of magnetite.

The percentage of nano-sized Fe particles was 1% by weight on the weight of the matrix (magnetite).

The nano-sized Fe particles were prepared according to the condensation process disclosed in U.S. Pat. No. 7,282,167. They comprised a Fe core and an iron-oxide coating and had average diameters from 15 to 25 nanometers.

The catalyst also contained 1% of Cu and 2% of K as promoters in percentages by weight on the weight of the support (magnetite).

The catalyst was introduced in a fixed bed reactor and then, under a condition of 320° C. and 20 bar, a syngas was flown at a SV (space velocity) of 500 vol./vol catalyst/hr.

The reaction products were determined by sending the gaseous phase of a sample to a GC (gas chromatograph) after cooling and separation of the liquid phase. The total amount of higher hydrocarbons in the liquid phase was determined by weighting.

The main reaction products were propene and ethylene. The selectivity for C2-C4 light-olefins was about 85% while the CO conversion was about 92%.

Example 2

Direct conversion of syngas to light-olefins was performed as in example 1 but with the difference that the catalyst contained K and MnO as promoters.

The content of said promoters was 2% MnO and 2% of K in percentages by weight on the weigh of the matrix.

The reaction products were determined by sending the gaseous phase of a sample to a GC (gas chromatograph) after cooling and separation of the liquid phase. The total amount of higher hydrocarbons in the liquid phase was determined by weighting.

The main reaction products were propene and ethylene. The selectivity for C2-C4 light-olefins was about 85% while the CO conversion was about 95%.

Example 3

Direct conversion of syngas to light-olefins was performed using a catalyst containing Fe (non nano-sized) particles precipitated from an aqueous solution containing Fe (III) nitrate on a support (matrix) consisting of magnetite.

The catalyst also contained 2% of MnO and 2% of K as promoters in percentages by weight on the weight of the support (magnetite).

The catalyst was activated prior to use by reduction under hydrogen atmosphere at normal pressure and 480° C. for 12 hours and it was tested in the same way as example 1.

The main reaction products were propene and ethylene. The selectivity for C2-C4 light-olefins was about 85% while the CO conversion was about 95%.

The invention claimed is:

1. A process for the production of C2-C4 olefins comprising the step of contacting syngas with a iron-based catalyst at a temperature in the range from 250° C. to 350° C. and at a pressure in the range from 10 bar to 40 bar, the catalyst including iron and/or iron oxide particles as active component arranged on a metal oxide support or matrix chosen from the group consisting of alumina, titania, silica, magnesium oxide, silica-alumina, ferrous materials and mixtures thereof,
   wherein said iron-based catalyst includes nano-sized Fe particles as active component which are dispersed on a support or matrix, said nano-sized Fe particles being Fe nano-particles, Fe alloy nano-particles, nano-particles having an iron or iron alloy core and an iron-oxide shell or mixtures thereof, and
   wherein the catalyst includes a promoter of the catalytic activity chosen from elements, molecules/compounds and combinations thereof including aluminium, potassium, calcium, magnesium, silicon, manganese and copper.

2. The process according to claim 1, wherein said nano-sized Fe particles have an iron or iron alloy core and an iron-oxide shell or mixtures thereof.

3. The process according to claim 1, wherein said nano-sized Fe particles are substantially spherical and have a diameter less than 50 nm.

4. The process according to claim 2, wherein the content of said nano-sized Fe particles is comprised between 1% and 5% by weight on the weight of the support or matrix.

5. The process according to claim 1, wherein the catalyst includes a Mn promoter and a K promoter.

6. The process according to claim 1, wherein the ferrous materials are selected from the group consisting of magnetite, wustite, cordierite and mixtures thereof.

7. The process according to claim 1, wherein said metal oxide support or matrix is magnetite.

8. The process according to claim 1, wherein said contacting step is carried out at a temperature from 300° C. to 350° C.

9. The process according to claim 1, wherein the syngas has a H2:CO molar ratio in the range from 1.5 to 2.5.

10. The process according to claim 1, wherein the catalyst includes one or more promoters in a percentage of 0.1-5% by weight on the weight of the support or matrix.

11. The process according to claim 1, further comprising the step of removing the reaction heat formed by the syngas conversion in a continuous or discontinuous way.

12. The process according to claim 3, wherein said nano-sized Fe particles are substantially spherical and have a diameter between 15 and 25 nm.

13. The process according to claim 3, wherein said nano-sized Fe particles are substantially spherical and have a diameter between 1 and 15 nm.

14. The process according to claim 5, wherein the catalyst includes MnO and a K promoter.

15. The process according to claim 9, wherein the syngas has a H2:CO molar ratio around 2:1.

* * * * *